(12) United States Patent
Carson et al.

(10) Patent No.: US 6,391,324 B2
(45) Date of Patent: May 21, 2002

(54) COSMETIC SKIN CARE COMPOSITIONS CONTAINING PULEGONE

(75) Inventors: Robert Carson, Rahway; Krupa Patel, Edison; Sreekumar Pillai, Wayne, all of NJ (US); Stewart Paton Granger, Turvey (GB)

(73) Assignee: Unilever Home & Personal Care USA, Division of Conopco, Greenwich, CT (US)

( * ) Notice: Subject to any disclaimer, the term of this patent is extended or adjusted under 35 U.S.C. 154(b) by 0 days.

(21) Appl. No.: 09/851,282

(22) Filed: May 8, 2001

Related U.S. Application Data
(60) Provisional application No. 60/202,602, filed on May 9, 2000.

(51) Int. Cl.[7] .............................. A61K 7/00; A61K 7/42
(52) U.S. Cl. ........................ 424/401; 424/59; 424/400; 514/844; 514/938
(58) Field of Search ................................ 424/400, 401, 424/59; 514/844, 938

(56) References Cited

U.S. PATENT DOCUMENTS

| | | | |
|---|---|---|---|
| 4,193,986 A | 3/1980 | Cox | 424/28 |
| 5,106,622 A | 4/1992 | Sherwood et al. | 424/195.1 |
| 5,128,135 A * | 7/1992 | Morimoto et al. | 424/443 |
| 5,466,452 A | 11/1995 | Whittle | 424/195.1 |
| 5,871,718 A | 2/1999 | Lucas et al. | 424/65 |
| 5,874,070 A | 2/1999 | Trinh et al. | 424/65 |
| 5,879,690 A * | 3/1999 | Perricone | 424/401 |

FOREIGN PATENT DOCUMENTS

| | | | |
|---|---|---|---|
| JP | 01135711 A | * | 5/1989 |
| JP | 08/143419 | | 6/1996 |
| WO | WO 98/00168 A1 | * | 1/1998 |

* cited by examiner

*Primary Examiner*—Jose G. Dees
*Assistant Examiner*—Marina Lamm
(74) *Attorney, Agent, or Firm*—Ellen Plotkin

(57) ABSTRACT

Cosmetic skin care compositions containing pulegone. The inventive compositions improve transglutaminase-1 expression and ceramide expression, and enhance the cell uptake of glucose.

9 Claims, No Drawings

COSMETIC SKIN CARE COMPOSITIONS CONTAINING PULEGONE

This application claims priority under 35 U.S.C. 119 from U.S. provisional application Ser. No. 60/202,602 filed May 9, 2000.

FIELD OF THE INVENTION

The present invention relates to compositions comprising pulegone and methods of improving the cosmetic appearance of the skin by topically applying such compositions to the skin.

BACKGROUND OF THE INVENTION

The human skin consists of two major layers: the dermis, the bottom thicker layer, and the epidermis, the top thinner layer. The dermis is the layer that provides strength, elasticity, and thickness to the skin. With aging, the thickness of the dermal layer is reduced, thus, partially causing the formation of wrinkles in aging skin. The top layer of the skin, the epidermis, provides the resilience and the barrier properties of the skin. The epidermis is composed of many different cell types. Keratinocytes are the major cell type of the epidermis, consisting of nearly 75 to 80% of the total number of cells in the human epidermis.

The keratinocytes reside in four distinct stages of differentiation within the epidermis. Epidermal differentiation is important to providing essential functions of the skin. Namely, epidermal differentiation aids the formation of a barrier layer that protects the body against the harmful substances in the environment and prevents loss of water from the body. Proper formation of the barrier layer of the epidermis requires skin cells to develop correctly through space and time and demands the synchronized production of essential lipid materials such as ceramides, cholesterol and fatty acids. Such lipid materials are formed by cells in the granular layer of the epidermis and are used to compose lipid layers that in turn become the skin's essential protective barrier layer. The lipid layers act as a water barrier to prevent water loss from the skin, and consequently, prevent the appearance of aged, dry, or wrinkled skin. As such, disruption of the skin's barrier layer and impairment of its functioning are associated with skin conditions such as atopic dermatitis, psoriasis, irritation and dry skin.

In normal skin, if the barrier function is disturbed, the epidermis re-synthesizes the deficient lipids. However, under certain conditions, a reduced capacity for re-synthesis may occur. Such is the case in aging or dry skin where skin lipid levels are in any case sub-normal and cell metabolism is impaired. Decreased uptake and utilization of glucose can lead to decreased metabolism and skin cell turnover, thereby leading to the appearance of aged, dry and flaky skin. Materials that enhance keratinocyte differentiation, increase lipid expression, or stimulate cell metabolism, may be useful in reversing such conditions to promote healthy skin.

Pulegone (5-Methyl-2-(1-methylethylidene) cyclohexanone) is an essential oil which may be found in pennyroyal, a naturally occurring plant. Prior art teaches the use of pulegone in applications such as pest repellants or perfumes. For example, U.S. Pat. No. 5,106,622 issued to Sherwood et al. cites the use of pennyroyal oil (~85% pulegone) in an insect repellent composition. U.S. Pat. No. 4,193,986 issued to Trinh et al. refers to the use of oil of pennyroyal as a component of a pest repellent for pets and animals. JP 08143419 refers to the use of pulegone in a bath composition for the purpose of repelling mites. U.S. Pat. No. 5,466,452 issued to Whittle refers to the use of extracts of Chinese herbs, some of which contain pulegone, for the preparation of materials to be taken orally or applied topically for relief of skin problems.

U.S. Pat. No. 5,871,718 issued to Lucas et al. and U.S. Pat. No. 5,874,070 issued to Trinh et al. disclose odor-absorbing compositions which may be used on skin. The compositions contain cyclodextrin, a molecule capable of complexing odor molecules. The compositions also include a perfume, which may be pulegone. Both patents teach that perfumes in the compositions (such as pulegone) tend to complex with cyclodextrins to reduce the concentration of the perfume actually delivered to the skin.

The prior art cited above does not disclose cosmetic compositions that can deliver solubilized pulegone to provide the combined benefit of enhanced differentiation and enhanced expression of lipids essential to barrier function. Therefore, a need exists for cosmetic compositions that can deliver pulegone to effectively improve the cosmetic appearance of skin.

SUMMARY OF THE INVENTION

The present invention relates to an oil in water emulsion of a cosmetic skin care composition comprising:

(a) from about 0.001% to about 10% of solubilized pulegone of Formula I:

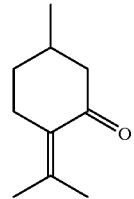

(b) a moisturizing agent; and
(c) a cosmetically acceptable vehicle.

DETAILED DESCRIPTION OF THE INVENTION

Except in the operating and comparative examples, or where otherwise explicitly indicated, all numbers in this description indicating amounts or ratios of material or conditions of reaction, physical properties of materials and/or use are to be understood as modified by the word "about." All amounts are by weight of the final composition, unless otherwise specified.

The term "skin" as used herein includes the skin on the face, neck, chest, back, arms, legs, hands, and scalp.

The term "solubilized" as used herein means that at least 90% of pulegone present in the final composition is solubilized.

An increase in transglutaminase-1 expression and ceramide expression can reduce dry skin by improving barrier formation as well as improving cell function and metabolism. Consequently, the appearance of lines, wrinkles, and aged skin are significantly reduced. Moreover, enhanced keratinocyte differentiation and lipid production and improved glucose uptake result in improved skin color, radiance, finish, and an overall healthy and youthful appearance of the skin. It is to such improvements that the present invention is directed.

According to the present invention, solubilized pulegone increases transglutaminase-1 expression (a marker for differentiation), ceramide expression, and glucose uptake.

All amounts are by weight of an oil-in-water emulsion, unless otherwise indicated.

Pulegone (5-Methyl-2-(1-methylethylidene) cyclohexanone) is an essential oil which is found in pennyroyal. Pulegone may be obtained from Sigma. Pulegone has the following structural formula I:

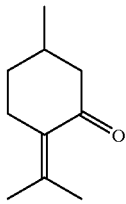

Pulegone must be solubilized and uncomplexed in order to deliver benefits to the skin. Particularly, solubilizing pulegone avoids evaporation of the pulegone within the composition before delivery into the skin. Moreover, if the pulegone is complexed, it is difficult to ensure that at least a minimum amount of pulegone is available for skin benefit. In a preferred embodiment, pulegone is incorporated in the inventive compositions in an amount of from 0.001% to 10%, preferably from 1% to 7%, and most preferably from 2% to 5%.

One fundamentally important criterion by which many topical lotions/creams must be measured is their ability to act as efficient skin moisturizers. Skin moisturizing ability is of extreme importance for topical lotions/creams in that consumers regard scaly, dry skin as unsightly and undesirable. Topical lotions that have the added benefit of enhancing skin moisture retention capabilities have a significant added benefit above and beyond the utility of their active ingredient. Thus, the inventive composition also comprises a moisturizing agent for imparting moisturizing characteristics and sensory benefits to the skin without impeding the benefits of pulegone on the skin.

The moisturizing agent of the present invention is selected so that the moisturizing agent does not get emulsified in the oil phase of an emulsion and therefore effectively deposits on the skin. Thus, the moisturizing agent is preferably water soluble to prevent emulsification within the inventive composition prior to application onto the skin. In the preferred embodiment, the moisturizing agent is selected from the group consisting of: propylene glycol, sorbitol, butylene, glycerin, cetostearyl alcohol, cetyl palmitate, myristyl alcohol, and palmitic alcohol, and mixtures thereof, due to commercial availability and water solubility. Most preferably, the moisturizing agent is selected from the group consisting of butylene and propylene glycol because both act as penetration enhancers to aid in delivering the solubilized pulegone in the inventive composition to the skin.

The moisturizing agent is selected from an amount of from 0.5% to 50%, preferably from 5% to 15%, and most preferably from 6% to 10% of the total composition, to enable maximum moisturing efficacy.

The composition according to the invention also comprises a cosmetically acceptable vehicle to act as a diluent, dispersant or carrier for pulegone in the composition, so as to facilitate its distribution when the composition is applied to the skin.

The inventive composition may be an oil-in-water or a water-in-oil emulsion. However, to provide maximum delivery, preferably the inventive composition is an oil-in-water emulsion, wherein pulegone is dissolved in the oil phase. The emulsion preferably contains at least 80 wt. % water, by weight of the vehicle. Preferably, the amount of water is at least 50 wt. % of the inventive composition, and most preferably from 60 to 80 wt. %, by weight of the composition.

Optional Skin Benefit Materials and Cosmetic Adjuncts

According to the present invention, among the beneficial effects of pulegone is its ability to enhance glucose uptake into skin cells. While pulegone enhances the uptake of endogenous glucose, the uptake may be further increased by adding an additional ingredient to the composition. Preferably, the ingredient is glucose or a compound that is known to break down in the skin to glucose since glucose is available for uptake without additional metabolism in the skin.

Compounds which break down in the skin to provide glucose include, but are not limited to, glucosamine, glucose glutamate, galactose, lactose, sucrose, and glucose phosphate esters.

This preferred optional ingredient is included in the inventive compositions in an amount of from 0.001% to 10%, preferably from 0.1% to 10%, most preferably from 0.1% to 5%.

Another category of functional ingredients within the cosmetic compositions of the present invention includes thickeners. A thickener will usually be present in amounts anywhere from 0.1% to 20% by weight, preferably from about 0.5% to 10% by weight of the composition. Exemplary thickeners are cross-linked polyacrylate materials available under the trademark Carbopol from the B. F. Goodrich Company. Gums may be employed such as xanthan, carrageenan, gelatin, karaya, pectin, and locust beans gum. Under certain circumstances the thickening function may be accomplished by a material also serving as a silicone or emollient. For instance, silicone gums in excess of 10 centistokes and esters such as glycerol stearate have dual functionality.

Powders may be incorporated into the cosmetic composition of the invention. These powders include chalk, talc, kaolin, starch, smectite clays, chemically modified magnesium aluminum silicate, organically modified montmorillonite clay, hydrated aluminum silicate, fumed silica, aluminum starch octenyl succinate and mixtures thereof.

The inventive compositions also preferably include sunscreens, perfumes and alpha hydroxy acids. Sunscreens aid in reducing the skin's exposure to harmful UV rays. Sunscreens include those materials commonly employed to block ultraviolet light. Illustrative compounds are the derivatives of PABA, cinnamate and derivatives of salicylate (other than ferulyl salicylate). For example, octyl methoxycinnamate and 2-hydroxy-4-methoxycinnamate and 2-hydroxy-4-methoxy benxophenone are commercially available under the trademarks, Parsol MCX and Bezonphenone-3, respectively. The exact amount of sunscreen employed in the emulsions can vary depending upon the degree of protection desired from the sun's UV radiation.

Other adjunct minor components may also be incorporated into the cosmetic composition. These ingredients may include coloring agents, and opacifiers. Amounts of these other adjunct minor components may range anywhere from 0.001% up to 20% by weight of the composition.

Product Use, Form, and Packaging

In use, a small quantity of the composition, for example from 1 to 100 ml, is applied to exposed areas of the skin, from a suitable container or applicator and, if necessary, it is then spread over and/or rubbed into the skin using the hand or fingers or a suitable device.

The cosmetic skin conditioning composition of the invention can be formulated as a lotion or a cream. The composition can be packaged in a suitable container to suit its viscosity and intended use by the consumer. For example, a lotion or cream can be packaged in a bottle, a roll-ball applicator, a propellant-driven aerosol device or a container fitted with a pump suitable for finger operation. When the composition is a cream, it can simply be stored in a non-deformable bottle or squeeze container, such as a tube or a lidded jar. The invention accordingly also provides a closed container containing a cosmetically acceptable composition as herein defined.

The following specific examples further illustrate the invention, but the invention is not limited thereto.

Materials and Methods

The final stage of epidermal differentiation is the formation of the cornified envelope. Transglutaminase, the enzyme responsible for the formation of cornified envelopes, is a marker of epidermal differentiation.

Keratinocyte Culture

Normal human keratinocytes, isolated from neonatal foreskin by trypsin treatment, were grown in Dulbecco's Modified Eagle's Medium (DMEM, Life Technologies, Grand Island, N.Y.) with 10% fetal bovine serum in the presence of irradiated mouse fibroblasts for establishing dividing keratinocyte colonies. Cells were incubated until their second passage and stored at $-70°$ C. for future use. All incubations took place at $37°$ C. with 5% $CO_2$. Frozen second passage keratinocytes were thawed and plated in T-175 flasks (Corning, Corning, N.Y.) with DMEM and grown for five days. After reaching 80% confluence, they were trypsinized and seeded into 6-well plates containing keratinocyte growth medium (KGM, Clonetics, San Diego, Calif.) with 0.15 mM calcium.

Transglutaminase (TG-1) Assay

A sample of the keratinocytes grown in the keratinocyte culture described above, were placed in KGM (2 ml per well) at 0.2 million cells/plate in 6-well plates and re-grown for five days until the cells reached approximately 20% confluence, since TG-1 only begins to become expressed after confluence. Two milliliters of fresh KGM were added to each well and 10 $\mu$l of corn oil containing 0, 2.5, 5 or 10% pulegone were placed on the surface of the medium each day for three days. One set of triplicate wells was left untreated to serve as control. After three days of incubation, cells were washed thoroughly with phosphate buffered saline (PBS, 10 mM sodium phosphate, 138 mM sodium chloride, 2.7 mM potassium chloride, pH 7.4) and placed at $-70°$ C. for 2 hours. Cells were then thawed for two hours. The DNA content of cells was quantified by using the DNA-binding fluorophore, bis-benzimidazole (Hoechst 33258) and measuring the specific fluorescence of the DNA-bound fluorophore (360 nm excitation, 450 nm emission). Cellular TG-1 levels were determined by using a transglutaminase-1 (TG-1) specific monoclonal antibody as the primary antibody (BC1, Amersham, UK) and a peroxidase labeled rabbit antimouse IgG as the secondary antibody (Amersham, UK). The plates were blocked at room temperature with 5% nonfat milk in Tris-buffered saline (TBS, 10 mM Tris, 150 mM NaCL, pH 8.0) for one hour followed by two hours incubation with the primary antibody (1:4000 dilution) in 1% milk/TBS at room temperature. After rinsing the plates three times with 1% milk/TBS containing 0.05% Tween 20 (Bio-Rad, Hercules, Calif.), the plates were incubated with a 1:4000 dilution of the secondary antibody at room temperature for two hours. The plates were then rinsed three times with 1% milk/0.05% Tween 20/TBS and three times with PBS. Color was developed by incubation with o-phenylene-diamine (Sigma, St. Louis, Mo.) and hydrogen peroxide (Sigma) dissolved in a 1:1 mixture of 0.2 M dibasic sodium phosphate (Sigma) and 0.1 M citric acid at pH 5.0(Sigma). Solutions were transferred to 4 mL plastic cuvets (Fisher Scientific, Pittsburgh, Pa.) and the absorbance was read at 492 nm on an Ultraspec 3000 spectrophotometer (Pharmacia, Piscataway, N.J.) and TG-1 levels were expressed as absorbence/DNA fluoroscence.

Lipid Analysis

A sample of the keratinocytes that were grown in the keratinocyte culture described above were placed in KGM (2 ml per well) at 0.2 million per 6-well plates and re-grown for five days until approximately 20% confluence was reached. Cells were fed and treated with pulegone as described above for the TG-1 Assay. After three days of treatment, cells were rinsed twice with PBS, then harvested by adding 3 ml of 0.1 N NaOH (Fisher) to each well and scraping with a rubber policeman. The supernatants were transferred to 16 mm×100 mm glass test tubes with teflon-coated caps and incubated for 1 hour at $70°$ C. After cooling to room temperature, a 50 $\mu$l aliquot was removed for protein determination (Pierce BCA assay, Rockford, Ill.). To each tube 320 $\mu$l of 1 N HCl and 2.5 ml of chloroform were added and the tubes mixed well. The tubes were then placed on a tumbler and agitated for thirty minutes. The mixtures were then centrifuged for 10 minutes at 2000×g. 2 mL of chloroform were removed from the organic phase and placed in an autosampler vial. The samples were then dried evaporated under $N_2$, resuspended in 60 $\mu$l of chloroform:methanol 2:1 and transferred to an autosampler insert microtube which was placed inside another autosampler vial whcih was sealed. 40 $\mu$l of the sample was spotted (Camag Automatic TLC Sampler III, Wilmington, N.C.) on silica TLC plates (Whatman 4807-700) and the plates were developed in horizontal chambers (Camag) using the following solvent system: 1. 95:4.5:0.5 chloroform, methanol, acetic acid and 2. 60:40:2 hexane, ethyl ether, acetic acid. Following immersion in 10% copper sulfate in 8% phosphoric acid, plates were charred at $165°$ C. for 20 minutes and then read in a densitometer (Camag TLC Scanner II). The results were expressed in ng cermaides/$\mu$g protein.

Glucose Uptake Assay

A sample of the keratinocytes grown in the keratinocyte culture described above, were plated in KGM medium at either 0.5 or 1 million cells/plate in six well plates and incubated for 4 days. The medium was then aspirated, and the wells were rinsed twice with Phosphate Buffered Saline (PBS), then the plates were incubated (1 mL/well) for 24 hours. The medium was replaced with fresh KBM, 10 $\mu$l of corn oil containing pulegone at various concentrations were added and cells were allowed to incubate (for 4 hours at $37°$ C.) before 2 $\mu$Ci of $^3$H 2-deoxy-glucose (Amersham, UK) were added to each well. Samples were then incubated for one hour. The medium was aspirated and wells were rinsed three times with PBS before the addition of 500 $\mu$L of 0.1N NaOH/well. After 10 minutes of agitation on a shaker, a 25 $\mu$L aliquot was removed for protein analysis, and 200 $\mu$L were transferred to a scintillation vial containing 5 mL Scintillation cocktail (Scintiverse) and counting was performed on a Beckman counter. $^3$H-Glucose uptake results were expressed as CPM/$\mu$g protein.

Concentrations used in the examples below are of pulegone in a corn oil droplet. The in vitro concentration may not be relevant to in vivo concentration because there is partitioning between the oil and the culture medium. The medium concentration of the active is not the oil droplet concentration of the active. For the pulegone to elicit its effect on the cultured cells, it must diffuse out of the corn oil into the culture medium where it is then accessible to the cells. The pulegone concentration in the culture medium is therefore considerably less than the concentration in the corn oil droplet.

EXAMPLE 1

This example investigated the effect of pulegone on transglutaminase expression in human keratinocytes, the results of which are summarized in Table 1.

TABLE 1

| SAMPLE | TG-1/DNA (Absorbance/ Arbitrary Units of DNA ± Standard Deviation) | % of CONTROL | P VALUE | STATISTICAL SIGNIFICANCE |
|---|---|---|---|---|
| CONTROL | 12.73 ± 1.41 | 100 | — | — |
| Pulegone 1% | 15.45 ± 2.32 | 121 | >0.05 | NO |
| Pulegone 2.5% | 24.96 ± 4.85 | 196 | <0.05 | YES |
| Pulegone 5% | 36.40 ± 0.89 | 286 | <0.05 | YES |

It can be seen from the results in Table 1 that human keratinocytes exposed to pulegone at 2.5% and 5% in corn oil had increased transglutaminase-1 expression in comparison to untreated keratinocytes.

EXAMPLE 2

This example investigated the effect of pulegone on ceramides expression in human keratinocytes, the results of which are summarized in Table 2.

TABLE 2

| SAMPLE | CERAMIDES (ng/μg PROTEIN ± S.D.) | % of CONTROL | P VALUE | STATISTICAL SIGNIFICANCE |
|---|---|---|---|---|
| CONTROL | 13.9 ± 3.60 | 100 | — | — |
| Pulegone 1% | 8.97 ± 1.17 | 65 | >0.05 | NO |
| Pulegone 2.5% | 23.8 ± 11.0 | 171 | >0.05 | NO |
| Pulegone 5% | 42.8 ± 6.91 | 308 | <0.05 | YES |

It can be seen from the results in Table 2 that human keratinocytes exposed to pulegone in corn oil increased expression of ceramides in comparison to untreated keratinocytes.

EXAMPLE 3

This example investigated the effect of pulegone on glucose uptake in human keratinocytes, the results of which are shown in Table 3.

TABLE 3

| SAMPLE | GLUCOSE UPTAKE (cpm/μg PROTEIN ± S.D.) | % of CONTROL | P VALUE | STATISTICAL SIGNIFICANCE |
|---|---|---|---|---|
| CONTROL | 4.83 ± 0.34 | 100 | — | — |
| Pulegone 1% | 3.71 ± 0.35 | 77 | <0.05 | YES |
| Pulegone 5% | 9.14 ± 0.69 | 189 | <0.05 | YES |

It can be seen from the results in Table 3 that human keratinocytes exposed to pulegone in corn oil significantly increased glucose uptake.

EXAMPLE 4

Example 4 illustrates topical compositions according to the present invention. The compositions can be processed in conventional manner. They are suitable for cosmetic use. In particular the compositions are suitable for application to wrinkled, rough, flaky, aged and/or UV-damaged skin and/or dry skin and post-menopausal skin to improve the appearance and the feel thereof as well as for application to healthy skin to prevent or retard deterioration thereof.

| INGREDIENT | % w/w |
|---|---|
| OIL-IN-WATER EMULSION | |
| Dl Water | 73.40 |
| Carbomer | 0.30 |
| Disodium EDTA | 0.10 |
| Glycerin | 3.00 |
| Polysorbate 20 | 2.50 |
| Butylene Glycol | 2.00 |
| Methylparaben | 0.30 |
| Triethanolamine 99% | 0.30 |
| Pulegone | 2.00 |
| Isopropyl Myristate | 5.00 |
| Octyl Palmitate | 3.00 |
| Cetyl Alcohol | 1.00 |
| Dimethicone, 100 cst | 0.50 |
| Beeswax | 0.30 |
| Propylparaben | 0.10 |
| Germall II | 0.10 |
| Fragrance | 0.10 |
| Total ----> | 100.00 |
| OIL-IN-WATER EMULSION | |
| Dl Water | 71.20 |
| Xanthan Gum | 0.20 |
| Disodium EDTA | 0.10 |
| Glycerin | 5.00 |
| Butylene Glycol | 2.00 |
| Methylparaben | 0.30 |
| Pulegone | 2.00 |
| Isopropyl Myristate | 5.00 |
| Octyl Palmitate | 3.00 |
| Cetyl Alcohol | 1.00 |
| Dimethicone, 100 cst | 0.50 |
| Steareth-2 | 0.40 |
| Steareth-21 | 3.00 |
| Propylparaben | 0.10 |
| Germall II | 0.10 |
| Fragrance | 0.10 |
| Total ----> | 100.00 |
| WATER-IN-OIL EMULSION | |
| Dl Water | 63.30 |
| Disodium EDTA | 0.10 |
| Glycerin | 3.00 |
| Propylene Glycol | 2.00 |
| Sodium Chloride | 0.70 |
| Methylparaben | 0.30 |
| Cyclomethicone | 14.00 |
| Pulegone | 2.00 |
| Isopropyl Myristate | 5.00 |
| Octyl Palmitate | 3.00 |
| Dimethicone Copolyol | 2.50 |
| Dimethicone, 100 cst | 0.50 |
| Beeswax | 0.30 |
| Propylparaben | 0.10 |
| Germall II | 0.10 |
| Fragrance | 0.10 |
| Total ----> | 100.00 |
| HYDRO-GEL | |
| Dl Water | 81.85 |
| Butylene Glycol | 5.00 |
| PPG-5-Ceteth 20 | 5.00 |
| Glycerin | 3.00 |
| Carbomer | 1.20 |
| Triethanolamine 99% | 1.20 |

-continued

| INGREDIENT | % w/w |
|---|---|
| Pulegone | 2.00 |
| Ascorbic acid | 1.00 |
| Methylparaben | 0.30 |
| Polysorbate 20 | 0.25 |
| Disodium EDTA | 0.10 |
| Germall II | 0.10 |
| Total ----> | 100.00 |
| ANHYDROUS SERUM | |
| Cyclomethicone | 72.40 |
| Pulegone | 1.00 |
| Isopropyl Myristate | 5.00 |
| Octyl Palmitate | 3.00 |
| Polyglycerol-6 Dioleate | 5.00 |
| Butylene Glycol | 4.00 |
| Dimethicone, 100 cst | 5.00 |
| Beeswax | 0.30 |
| Propylparaben | 0.20 |
| Fragrance | 0.10 |
| Total ----> | 100.00 |
| HYDRO-ALCOHOLIC GEL | |
| DI Water | 52.85 |
| Alcohol SDA40B | 30.00 |
| Butylene Glycol | 5.00 |
| PPG-5-Ceteth 20 | 5.00 |
| Glycerin | 3.00 |
| Carbomer | 1.20 |
| Triethanolamine 99% | 1.20 |
| Pulegone | 1.00 |
| Methylparaben | 0.30 |
| Polysorbate 20 | 0.25 |
| Disodium EDTA | 0.10 |
| Germall II | 0.10 |
| Total ----> | 100.00 |

It should be understood that the specific forms of the invention herein illustrated and described are intended to be representative only. Changes, including but not limited to those suggested in this specification, may be made in the illustrated embodiments without departing from the clear teachings of the disclosure. Accordingly, reference should be made to the following appended claims in determining the full scope of the invention.

What is claimed is:

1. An oil in water emulsion of a cosmetic skin care composition essentially of:

(a) from about 0.001% to about 10% of solubilized pulegone of Formula I:

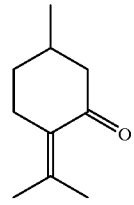

(b) a glucose compound or a compound known to break down in the skin to glucose;
  (c) a moisturizing agent; and
  (d) a cosmetically acceptable vehicle.

2. The composition of claim 1 wherein the moisturizing agent is selected from the group consisting of: propylene glycol, sorbitol, butylene, glycerin, cetostearyl alcohol, cetyl palmitate, myristyl alcohol, and palmitic alcohol, and mixtures thereof.

3. The composition of claim 1 wherein said glucose compound is selected from the group consisting of glucose, glucosamine, glucose glutamate, galactose, lactose, sucrose and glucose phosphate esters.

4. The composition of claim 1 further comprising a cosmetically beneficial ingredient selected from the group consisting of sunscreen, perfumes, and alpha hydroxy acids.

5. A cosmetic method of treating aged, photoaged, dry, lined or wrinkled skin, the method comprising the step of applying to the skin the composition according to claim 1.

6. A cosmetic method of improving the barrier function of the skin, the method comprising applying to the skin the composition according to claim 1.

7. A cosmetic method of improving keratinocyte differentiation, the method comprising applying to the skin the composition according to claim 1.

8. A cosmetic method of improving the lipid production by keratinocytes, the method comprising applying to the skin the composition according to claim 1.

9. A cosmetic method of improving the glucose uptake by keratinocytes, the method comprising applying to the skin the composition according to claim 1.

* * * * *